(12) United States Patent
Yamada et al.

(10) Patent No.: US 8,357,815 B2
(45) Date of Patent: Jan. 22, 2013

(54) METAL COMPOUND, MATERIAL FOR CHEMICAL VAPOR PHASE GROWTH, AND PROCESS FOR FORMING METAL-CONTAINING THIN FILM

(75) Inventors: Naoki Yamada, Tokyo (JP); Atsuya Yoshinaka, Tokyo (JP); Senji Wada, Tokyo (JP)

(73) Assignee: Adeka Corporation, Tokyo (JP)

( * ) Notice: Subject to any disclaimer, the term of this patent is extended or adjusted under 35 U.S.C. 154(b) by 451 days.

(21) Appl. No.: 12/740,188

(22) PCT Filed: Oct. 22, 2008

(86) PCT No.: PCT/JP2008/069121
§ 371 (c)(1),
(2), (4) Date: Apr. 28, 2010

(87) PCT Pub. No.: WO2009/093366
PCT Pub. Date: Jul. 30, 2009

(65) Prior Publication Data
US 2010/0247765 A1 Sep. 30, 2010

(30) Foreign Application Priority Data

Jan. 25, 2008 (JP) .................................. 2008-014791

(51) Int. Cl.
*C07F 7/00* (2006.01)
*C23C 16/00* (2006.01)
(52) U.S. Cl. ........................ 556/51; 106/1.25; 427/248.1
(58) Field of Classification Search .................... 556/51; 427/248.1; 106/1.25
See application file for complete search history.

(56) References Cited

FOREIGN PATENT DOCUMENTS

| JP | 07-201779 | 8/1995 |
|---|---|---|
| JP | 2000-036473 | 2/2000 |
| JP | 2003-064475 | 3/2003 |
| JP | 2006-045083 | 2/2006 |
| JP | 2006-182709 | 7/2006 |
| KR | 10-0156980 | 12/1998 |

OTHER PUBLICATIONS

International Search Report dated Mar. 5, 2012, Application No. 201002555-9.
Siddhartha Panda et al., Low Temperature Chemical Vapor Deposition of Titanium Nitride Films from Tetrakis (Ethylmethylamido) Titanium and Ammonia, Thin Solid Films, vol. 357, Issue 2, Dec. 15, 1999, pp. 125-131.
International Search Report, PCT/JP2008/069121, Dec. 2, 2008.

*Primary Examiner* — Porfirio Nazario Gonzalez
(74) *Attorney, Agent, or Firm* — Young & Thompson

(57) ABSTRACT

A novel metal compound of general formula (1), a material for chemical vapor phase growth containing the compound, and a process for forming a metal-containing thin film by chemical vapor phase growth using the material. Among the compounds of formula (1), those wherein X is a chlorine atom are preferred because of inexpensiveness and high volatility. When M is titanium, those wherein m is 1 are preferred as having a greater difference between a volatilization temperature (vapor temperature) and a deposition temperature (reaction temperature), which provides a broader process margin.

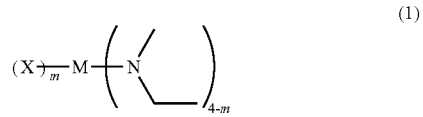

(1)

In formula (1), M is titanium, zirconium, or hafnium; X is a halogen atom; and m is 1 or 2.

16 Claims, 1 Drawing Sheet

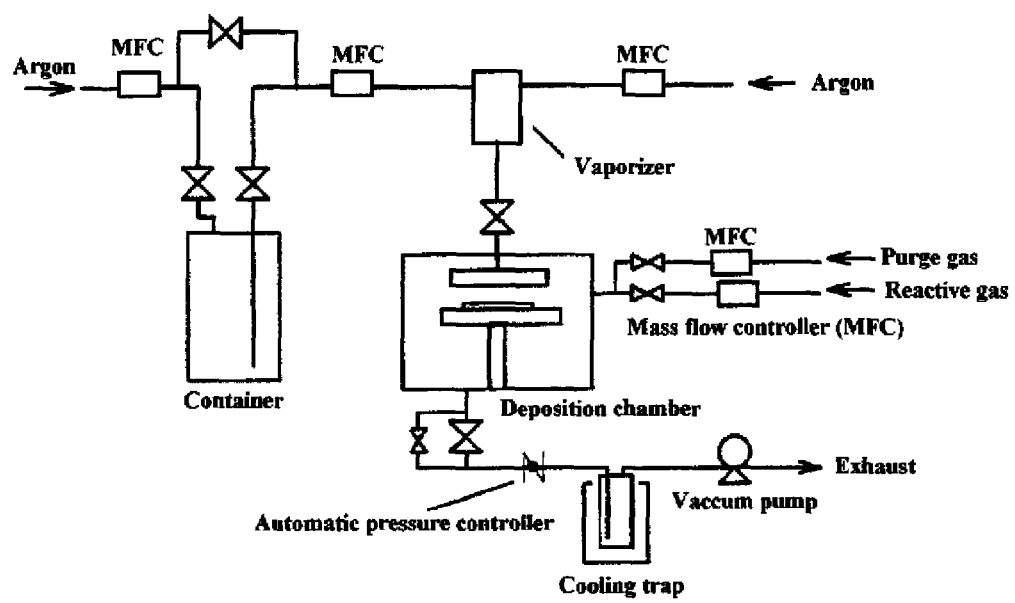

METAL COMPOUND, MATERIAL FOR CHEMICAL VAPOR PHASE GROWTH, AND PROCESS FOR FORMING METAL-CONTAINING THIN FILM

TECHNICAL FIELD

This invention relates to a novel metal compound having a specific structure, a material for chemical vapor phase growth containing the metal compound, and a process for fabricating a metal-containing thin film using the material.

BACKGROUND ART

A thin film containing titanium, zirconium, or hafnium is used as an electronic member of electronic components, such as high dielectric constant capacitors, ferroelectric capacitors, gate films, barrier films, and gate insulators, and an optical element of optical communication devices, such as optical waveguides, optical switches, and optical amplifiers.

Processes for forming the above-described thin film include MOD techniques including a dipping-pyrolysis process and a sol-gel process and chemical vapor-phase growth techniques, such as chemical vapor deposition (hereinafter abbreviated as CVD) and atomic layer deposition (hereinafter abbreviated as ALD). Chemical vapor phase growth techniques involving vaporization of a precursor, such as CVD and ALD, are the most suitable for many advantages, such as compositional controllability, excellent step coverage, suitability to large volume production, and capability of hybrid integration. Metal compounds having an organic ligand are used as a precursor in CVD or ALD.

Metal nitride thin films having titanium, zirconium, or hafnium as a metal are used as a coating layer for enhancing the hardness and strength of, e.g., cutting tools, and gate films and barrier films of semiconductor devices. A number of techniques for fabricating these thin films by chemical vapor phase growth have been reported.

Patent document 1 (see below) discloses a process for forming a metal nitride and/or metal carbide thin film using a halide of titanium, zirconium, hafnium, vanadium, niobium, or tantalum. Patent document 2 (see below) describes a CVD process for forming a thin film of titanium nitride using titanium tetrachloride and ammonia gas.

Patent documents 3 to 5 propose processes for depositing a group 4 metal-containing thin film using, as a titanium, zirconium or hafnium precursor, a dialkylaminometal compound having an organic amine as a ligand, disclosing use of ethylmethylamine as the ligand.

However, the film formation process using a chloride typified by titanium tetrachloride needs high temperatures of at least about 500° C. Such a high temperature is unsuitable in the production of a semiconductor device element, such as a gate film. Although the organic amide metal compound having an organic amine as a ligand is capable of forming a metal nitride thin film at low temperatures, it is difficult for the resulting film to exhibit electrical characteristics as expected because of its high residual carbon content and to be applied to a gate film, a barrier film, or an electrode film that are particularly required to have electrical conductivity.

Patent document 6 (see below) teaches a process for forming a titanium nitride thin film by CVD using $Ti(N(CH_3)_2)_3X$, $Ti(N(CH_3)_2)_2X_2$, $Ti(N(C_2H_5)_2)_3X$, or $Ti(N(C_2H_5)_2)_2X_2$ (wherein X is a halogen atom). These titanium compounds are described as being easily thermally decomposable and suited for use as a gate film forming material. However, $Ti(N(CH_3)_2)_3Cl$ and $Ti(N(CH_3)_2)_2Cl_2$, which are representatively used in patent document 6, are solid and need to be maintained at a temperature at or above the melting point when used as a CVD material. They, while having good thermal decomposability, have poor thermal stability and can decompose during being heated to be kept in a liquid state for a long period of time. If used as it is a solid, there arise problems with the material vapor feed and in-line transportation of the material, such as shortage of vapor feed or variation in vapor feed with time. The problem of contamination with particles also occurs. Even in a process using a solution, such as a solution CVD process using a solution of a solid precursor in an organic solvent, the solution suffers from precipitation due to change in temperature, partial evaporation of the solvent, and change in concentration in a vaporizer, resulting in clogging of feed piping. The problem of the feed rate change with time due to, e.g., clogging of feed piping and the problem of contamination with particles remain to be completely settled down.

Patent document 1: JP 2003-64475A
Patent document 2: JP 7-201779A
Patent document 3: Korean Patent 156980
Patent document 4: JP 2006-45083A
Patent document 5: JP 2006-182709A
Patent document 6: JP 2000-36473A

DISCLOSURE OF THE INVENTION

Problem to be Solved by the Invention

An object of the invention is to provide a metal compound capable of forming a metal-containing thin film with reduced residual carbon and establishing a process assuring a stable deposition rate and stable film composition control. As used herein, the term "material for chemical vapor phase growth", which will be also referred to as "chemical vapor phase growth material", refers to both a material for CVD and a material for ALD unless otherwise specified.

Means for Solving the Problem

As a result of extensive investigations, the present inventors have found that a metal compound having a specific structure accomplishes the above object of the invention.

The invention provides a metal compound represented by general formula (1):

[Formula 1]

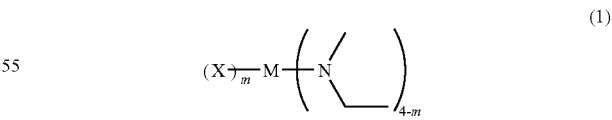

wherein M represents titanium, zirconium, or hafnium; X represents a halogen atom; and m represents 1 or 2.

The invention also provides a material for chemical vapor phase growth that contains the metal compound.

The invention also provides a process for forming a metal-containing thin film by chemical vapor phase growth characterized by using the material for chemical vapor phase growth.

BEST MODE FOR CARRYING OUT THE INVENTION

The invention will be described in detail based on its preferred embodiments.

The metal compound of the invention is a novel compound represented by general formula (1) shown above.

In general formula (1), examples of the halogen atom as represented by X include fluorine, chlorine, bromine, and iodine. Among the compounds of formula (1), preferred are those wherein X is a chlorine atom because of high volatility and inexpensiveness of raw materials for making them.

Compounds of formula (1) wherein m is 1 are more volatile than those wherein m is 2, and those wherein m is 2 have a lower thermal decomposition temperature than those wherein m is 1. For use as a chemical vapor phase growth material, those having a greater difference between a volatilization temperature (vapor temperature) and a deposition temperature (reaction temperature) are convenient because of the provision of a broader process margin. Accordingly, m is preferably selected so as to afford a broader process margin. When M is titanium, for example, those in which m is 1 are preferred as providing a larger process margin.

A compound represented by $Cl_nTi(N(CH_3)_2)_{4-n}$ (n=1 or 2), which is analogous to the compound of formula (1) wherein X is a chlorine atom, and M is titanium, is a solid having a melting point of 70° to 95° C., whereas the analogous compound of the invention is liquid and particularly suited for use as a chemical vapor phase growth material.

Examples of the metal compound of the invention include compound Nos. 1 through 24 below.

[Formula 2]

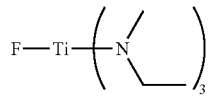

Compound No. 1

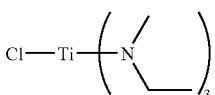

Compound No. 2

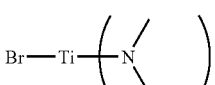

Compound No. 3

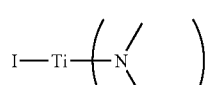

Compound No. 4

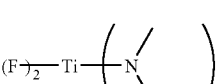

Compound No. 5

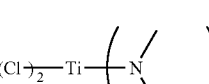

Compound No. 6

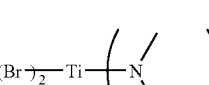

Compound No. 7

[Formula 3]

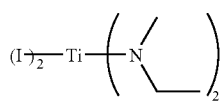

Compound No. 8

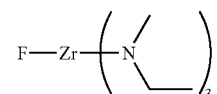

Compound No. 9

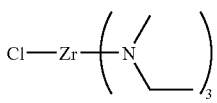

Compound No. 10

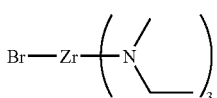

Compound No. 11

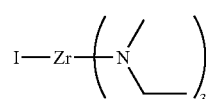

Compound No. 12

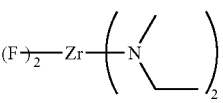

Compound No. 13

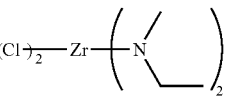

Compound No. 14

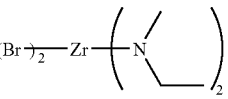

Compound No. 15

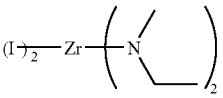

Compound No. 16

[Formula 4]

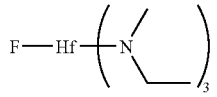

Compound No. 17

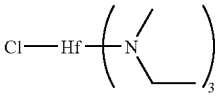

Compound No. 18

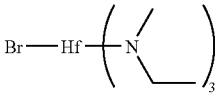

Compound No. 19

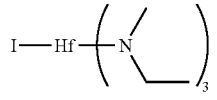

Compound No. 20

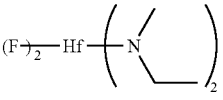

Compound No. 21

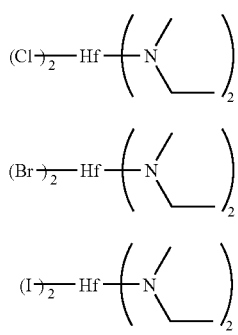

Compound No. 22

Compound No. 23

Compound No. 24

The metal compound of the invention is not limited by the process of preparation and can be prepared by using well-known reactions. Useful processes include the reaction between $MX_4$ (wherein M and X are as defined above) and ethylmethylamine of an amount necessary to afford a desired number m and the reaction between $MX_4$ and $M(NEtMe)_4$ of an amount necessary to afford a desired number m. The former reaction is preferably carried out by converting an alkyl lithium as a starting compound to ethylmethylaminolithium as an intermediate, which is then allowed to react with $MX_4$. The latter reaction is preferably performed by mixing $MX_4$ and $M(NEtMe)_4$ and stirring the mixture at a temperature necessary to effect the reaction. The preparation of the metal compound of the invention is conducted in an environment as free as possible from any reactive species, such as water, oxygen, and carbon dioxide.

The material for chemical vapor phase growth according to the invention comprises the metal compound of general formula (1) as a thin film precursor. The form of the material is selected as appropriate to the procedures of chemical vapor phase growth employed, such as a source delivery system.

The source delivery system includes a vapor delivery system in which a chemical vapor phase growth material is vaporized by heating and/or pressure reduction in a container and introduced into a deposition reaction chamber, if desired, together with a carrier gas, e.g., argon, nitrogen or helium, and a liquid delivery system in which a chemical vapor phase growth material is delivered in the form of a liquid or a solution to a vaporizer, where it is vaporized by heating and/or pressure reduction and then led to a deposition reaction chamber. When applied to the vapor delivery system, the metal compound represented by general formula (1) per se is the chemical vapor phase growth material. In the case of the liquid delivery system, the metal compound of formula (1) per se or a solution of the metal compound in an organic solvent is the chemical vapor phase growth material.

In a multi-component chemical vapor phase growth process used to fabricate a multi-component thin film, the source delivery systems includes a system in which a plurality of the materials are separately vaporized and delivered (hereinafter referred to as a multi-source system) and a system in which a plurality of the materials are previously mixed at a prescribed ratio, and the mixture is vaporized and delivered (hereinafter referred to as a single source system). In the case of the single source system, the material for chemical vapor phase growth may be a mixture of the metal compounds of formula (1) or a solution of the mixture in an organic solvent or a mixture of the metal compound(s) of formula (1) and other precursor(s) or a solution of the mixture in an organic solvent.

The organic solvent that can be used in the material for chemical vapor phase growth is not particularly limited, and any widely known organic solvent that is inert to the metal compound of the invention may be used. Examples of useful organic solvents include acetic esters, such as ethyl acetate, butyl acetate, and methoxyethyl acetate; ethers, such as tetrahydrofuran, tetrahydropyran, morpholine, ethylene glycol dimethyl ether, diethylene glycol dimethyl ether, triethylene glycol dimethyl ether, dibutyl ether, and dioxane; ketones, such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons, such as hexane, cyclohexane, methylcyclohexane, dimethylcyclohexane, ethylcyclohexane, heptane, octane, toluene, and xylene; hydrocarbons having a cyano group, such as acetonitrile, 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine, and lutidine. A solvent or a mixture of solvents to be used is selected according to, for example, solubility for the solute and the boiling temperature or ignition temperature in relation to the working temperature. In using these organic solvents, the total concentration of the metal compound(s) of the invention in the organic solvent is preferably 0.01 to 2.0 mol/l, still preferably 0.05 to 1.0 mol/l.

Other precursors that can be used in combination with the metal compound of formula (1) in the multi-component chemical vapor phase growth process using a multi-source system or a single source system are not particularly limited, and any precursors well-known in the art may be used.

Examples of the other precursors include compounds formed between silicon, boron, phosphorus, or a metal and one or more organic coordinating compounds selected from alcohol compounds, glycol compounds, β-diketone compounds, cyclopentadiene compounds, organic amine compounds, and so forth. The metal species include the Group 1 elements, such as lithium, sodium, potassium, rubidium, and cesium; the Group 2 elements, such as beryllium, magnesium, calcium, strontium, and barium; the Group 3 elements, such as scandium, yttrium, lanthanoid elements (i.e., lanthanum, cerium, praseodymium, neodymium, promethium, samarium, europium, gadolinium, terbium, dysprosium, holmium, erbium, thulium, ytterbium, and lutetium), and actinoid elements; the Group 4 elements, such as titanium, zirconium, and hafnium; the Group 5 elements, such as vanadium, niobium, and tantalum; the Group 6 elements, such as chromium, molybdenum, and tungsten; the Group 7 elements, such as manganese, technetium, and rhenium; the Group 8 elements, such as iron, ruthenium, and osmium; the Group 9 elements, such as cobalt, rhodium, and iridium; the Group 10 elements, such as nickel, palladium, and platinum; the Group 11 elements, such as copper, silver, and gold; the Group 12 elements, such as zinc, cadmium, and mercury; the Group 13 elements, such as aluminum, gallium, indium, and thallium; the Group 14 elements, such as germanium, tin, and lead; and the Group 15 elements, such as arsenic, antimony, and bismuth; and the Group 16 elements, such as polonium.

The alcohol compounds that can be used as an organic ligand include alkyl alcohols, such as methanol, ethanol, propanol, isopropanol, butanol, 2-butanol, isobutanol, tert-butanol, amyl alcohol, isoamyl alcohol, and tert-amyl alcohol; ether alcohols, such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-sec-butoxy-1,1-diethylethanol, and 3-methoxy-1,1-dimethylpropanol; and dialkylamino alcohols providing the alkoxide compounds of the invention.

The glycol compounds that can be used as an organic ligand include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol.

The β-diketone compounds that can be used as an organic ligand include alkyl-substituted β-ketones, such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione, 2-methyl-6-ethyldecane-3,5-dione, and 2,2-dimethyl-6-ethyldecane-3,5-dione; fluoroalkyl-substituted β-diketones, such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; and ether-substituted β-diketones, such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

The cyclopentadiene compounds that can be used as an organic ligand include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, dimethylcyclopentadiene, tetramethylcyclopentadiene, and pentamethylcyclopentadiene.

The organic amine compounds that can be used as an organic ligand include methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, and isopropylmethylamine.

The other precursor, when used in a multi-source system, is preferably a compound that exhibits similar behavior in reaction or decomposition into a thin film composition. When used in ALD, the other precursor is preferably a compound reactive with the formed atomic layer (the layer of the metal compound of the invention or an intermediate layer resulting from the reaction of the metal compound layer). When used in a single-source system, the other precursor is preferably a compound that undergoes no modification due to chemical reaction on mixing as well as exhibits similar behavior in conversion to a thin film composition.

If desired, the material for chemical vapor phase growth of the invention may contain a nucleophilic reagent to stabilize the metal compound of the invention and other precursor. Examples of the nucleophilic reagent include ethylene glycol ethers, such as glyme, diglyme, triglyme, and tetraglyme; crown ethers, such as 18-crown-6, dicyclohexyl-18-crown-6, 24-crown-8, dicyclohexyl-24-crown-8, and dibenzo-24-crown-8; polyamines, such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyl-triethylenetetramine, and triethoxytriethyleneamine; cyclic polyamines, such as cyclam and cyclen; and heterocyclic compounds, such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane. The nucleophilic reagent as a stabilizer is used in an amount of 0.05 to 10 mol, preferably 0.1 to 5 mol, per mole of the metal compound of the invention.

The chemical vapor phase growth material of the invention should have minimized contents of impurities other than the constituent components, including impurity metal elements, impurity halogens (e.g., impurity chlorine), and impurity organic matter. The impurity metal element content is preferably 100 ppb or less, more preferably 10 ppb or less, for every element, and a total impurity metal content is preferably 1 ppm or less, more preferably 100 ppb or less. In particular, in the fabrication of a thin film of a metal oxide, a silicon-containing metal complex oxide, a nitride, a silicon-containing oxynitride, or the like for use as a gate insulator film, a gate film, or a barrier film of LSI devices, it is required to minimize the contents of alkali metal elements, alkaline earth metal elements, and congeners of titanium, zirconium, or hafnium that are influential on the electrical characteristics of the resulting thin film. The impurity halogen content is preferably 100 ppm or less, more preferably 10 ppm or less, even more preferably 1 ppm or less. The total impurity organic matter content is preferably 500 ppm or less, more preferably 50 ppm or less, even more preferably 10 ppm or less. A water content causes particle generation in the CVD material or during chemical vapor phase growth. Therefore, it is advisable to previously remove the water content from the metal compound, the organic solvent, and the nucleophilic reagent as much as possible before use. The water content of each of the metal compound, organic solvent, and nucleophilic reagent is preferably 10 ppm or less, more preferably 1 ppm or less.

In order to reduce or prevent contamination of a thin film with particles, it is desirable for the chemical vapor phase growth material of the invention to have not more than 100 particles greater than 0.3 μm, more desirably not more than 1000 particles greater than 0.2 μm, even more desirably not more than 100 particles greater than 0.2 μm, per ml of its liquid phase as measured with a light scattering particle sensor for detecting particles in a liquid phase.

The process of forming a thin film according to the present invention is a chemical vapor phase growth process, in which a vaporized material of the metal compound (precursor) of the invention and, if necessary, other precursor, and, if necessary, a reactive gas are led to a substrate, and the precursor(s) is/are allowed to decompose and/or chemically react on the substrate to make a thin film grow and build up on the substrate. The process of the present invention is not particularly restricted by the material delivery system, the mode of deposition, the film formation conditions, the film formation equipment, and the like. Any conditions and methods commonly known in the art are made use of.

Examples of the reactive gas that may be used if desired include those for the formation of an oxide film, such as oxidizing gases, such as oxygen, ozone, nitrogen dioxide, nitrogen monoxide, water vapor, hydrogen peroxide, formic acid, acetic acid, and acetic anhydride; and reducing gases, such as hydrogen. Reactive gases that can be used to form a nitride film include organic amine compounds, such as monoalkylamines, dialkylamines, trialkylamines, and alkylenediamines; hydrazine, ammonia, and nitrogen.

The material delivery systems include the above-described vapor delivery system, liquid delivery system, multi-source system, and single source system.

The deposition modes include thermal CVD (only heat is used to cause the vaporized material or a mixture of the vaporized material and a reactive gas to react to deposit a film), plasma-enhanced CVD (heat and plasma are used), photo-assisted CVD (heat and light are used), photo plasma-assisted CVD (heat, light, and plasma are used), and ALD (Atomic Layer Deposition) in which a deposition reaction of CVD is divided into elementary reaction steps so as to build up a film stepwise on a molecular level.

The film formation conditions include reaction temperature (the substrate temperature), reaction pressure, and deposition rate. The reaction temperature is preferably 150° C. or higher at which the metal compound of the invention reacts sufficiently, more preferably 250° to 450° C. The reaction pressure is from atmospheric pressure to 10 Pa for thermal CVD and photo-assisted CVD or from 10 to 2000 Pa for film formation using plasma. The deposition rate can be controlled by the material feed conditions (vaporizing temperature and vaporizing pressure) and the reaction temperature and pressure. Too high a deposition rate tends to result in deteriorated characteristics of the resulting thin film, and too low a deposition rate can result in poor productivity. A preferred deposition rate ranges from 0.5 to 5000 nm/min, more preferably 1 to 1000 nm/min. In the case of ALD, the film thickness is controlled by the number of cycles to reach a desired film thickness. The thickness of the thin film fabricated of the chemical vapor phase growth material of the invention is preferably selected from the range of 0.1 to 1000 nm, while varying depending on the intended use.

The metal compound of the invention affords a metal nitride with little impurity, such as residual carbon, and is therefore preferably used to form a metal nitride thin film. A preferred process for forming a metal nitride thin film using the chemical vapor phase material of the invention is ALD. ALD is a process in which a chemical vapor phase growth material and, if necessary, a reactive gas, and other precursor are alternately pulsed to make one cycle to form an atomic monolayer, and this cycle is repeated until the atomic layers are deposited and built up to a desired thickness. In each cycle, the pulse of the vapor phase growth material and/or the reactive gas may optionally be followed by a step of removing the unreacted vapor phase growth material and/or the unreacted reactive gas by purging with an inert gas and/or by evacuation. ALD is characterized by providing a thin film with a smaller and more uniform thickness than CVD processes. Another advantage of ALD, from the nature of the film formation mechanism, is a lower deposition temperature required. This advantage makes ALD widely applicable independently of the heat resistance of a substrate, diffusivity of the element to a substrate, and the like. ALD may be effected in combination with heat, light, or plasma.

In the film formation process of the present invention, the resulting thin film may be subjected to annealing in an inert atmosphere, an oxidative atmosphere, or a reducing atmosphere to obtain improved electrical characteristics. Where step coverage is required, the process may include the step of reflowing the thin film. The temperature for annealing or reflowing should be within a range permissible for the use of the thin film. The temperature is usually from 300 to 1200° C., preferably 400 to 600° C.

Combined with appropriate selections of a precursor of other component, a reactive gas, and film forming conditions, the chemical vapor phase growth material of the invention and the thin film formation process using the material provide a thin film of desired kind, such as metal oxide films, metal nitride films, and glass. Examples of the composition of metal oxide films include titanium oxide, zirconium oxide, hafnium oxide, bismuth-titanium complex oxide, a bismuth-rare earth element-titanium complex oxide, silicon-titanium complex oxide, silicon-zirconium complex oxide, silicon-hafnium complex oxide, hafnium-aluminum complex oxide, a hafnium-rare earth element complex oxide, silicon-bismuth-titanium complex oxide, silicon-hafnium-aluminum complex oxide, a silicon-hafnium-rare earth element complex oxide, titanium-zirconium-lead complex oxide, titanium-lead complex oxide, strontium-titanium complex oxide, barium-titanium complex oxide, and barium-strontium-titanium complex oxide. Examples the composition of metal nitride films include titanium nitride, zirconium nitride, hafnium nitride, titanium-aluminum complex nitride, silicon-hafnium complex oxynitride (HfSiON), and a titanium complex oxynitride. Applications of these films include members of electronic components, such as high dielectric constant capacitor films, gate insulators, gate films, electrode films, barrier films, ferroelectric capacitor films, and condenser films; and optical glass members, such as optical fibers, optical waveguides, optical amplifiers, and optical switches.

EXAMPLES

The present invention will now be illustrated in greater detail with reference to Examples, Evaluation Example, and Comparative Example, but it should be understood that the invention is not construed as being limited thereto.

Example 1

Preparation of Compound No. 2

A reaction flask was charged with 43.0 g of titanium tetrachloride ($TiCl_4$) and 500 ml of dehydrated hexane and cooled to −10° C. in a dry argon atmosphere. A mixed solution of 191 g of tetrakis(ethylmethylamino)titanium ($Ti[N(CH_3)(C_2H_5)]_4$) and 500 ml of dehydrated hexane was added thereto dropwise in a manner such that the reaction system temperature might not exceed −5° C. Completion of the dropwise addition was followed by stirring at room temperature for 8 hours. Hexane was removed by evaporation under reduced pressure, and the residue was distilled under reduced pressure. From a fraction collected at a distillation temperature of 82° C. under a pressure of 100 Pa was obtained compound No. 2 in a yield of 90%. Identification of the compound was accomplished by elemental analysis and $^1$H-NMR analysis. The results of the analyses are shown below.

(1) Elemental analysis (metal analysis via atomic absorption/chloride analysis via silver nitrate titration)
Ti: 18.5 mass % (theoretical: 18.59 mass %)
Cl: 13.4 mass % (theoretical: 13.76 mass %)
(2) $^1$H-NMR (solvent: deuterobenzene) (chemical shift: multiplicity:number of hydrogens)
(3.096:s:3) (3.429:q:2) (1.003:t:3)

Example 2

Preparation of compound No. 6

A reaction flask was charged with 55.7 g of titanium tetrachloride ($TiCl_4$) and 300 ml of dehydrated toluene and cooled to −10° C. in a dry argon atmosphere. A mixed solution of 82.3 g of tetrakis(ethylmethylamino)titanium ($Ti[N(CH_3)(C_2H_5)]_4$) and 300 ml of dehydrated toluene was added thereto dropwise in a manner such that the reaction system temperature might not exceed −5° C. Completion of the dropwise addition was followed by stirring at room temperature for 8 hours. Toluene was removed by evaporation under reduced pressure, and the residue was distilled under reduced pressure. From a fraction collected at a distillation temperature of 85° C. under a pressure of 100 Pa was obtained compound No. 6 in a yield of 90%. Identification of the compound was accomplished by elemental analysis and $^1$H-NMR analysis. The results of the analyses are shown below.

(1) Elemental analysis (metal analysis via atomic absorption/chloride analysis via silver nitrate titration)

Ti: 20.3 mass % (theoretical: 20.38 mass %)

Cl: 30.1 mass % (theoretical: 30.17 mass %)

(2) $^1$H-NMR (solvent: deuterobenzene) (chemical shift: multiplicity:number of hydrogens)

(3.021:s:3) (3.470:q:2) (1.003:t:3)

Evaluation Example

Compound Nos. 2 and 6 prepared in Examples 1 and 2 and the comparative compounds shown in Tables 1 and 2 were evaluated in terms of the state at 20° C. and thermal decomposability. A compound that was solid at 20° C. was further analyzed for melting point (DTA onset melting temperature). The results obtained are shown in Tables 1 and 2. The thermal decomposability was expressed as the heating temperature at which a test compound sealed in a stainless steel container was heated for one hour to produce more than 0.5 mass % of a decomposition product as determined by TG-DTA under reduced pressure (10 ton). The heating temperature employed for compounds other than $TiCl_4$ was raised from 80° C. up to 200° C. by 10° C. The heating temperature for $TiCl_4$ was selected from the range of 250 to 300° C. When, for example, the results of TG-DTA under reduced pressure after one hour heating at 130° C. revealed vaporization of almost the whole amount of a compound while the results of TG-DTA under reduced pressure after one hour heating at 140° C. showed that the compound did not completely volatilize but left a residue of more than 0.5 mass % at the completion of mass loss, the thermal decomposability of the compound was regarded as 140° C.

TABLE 1

| Metal Compound | State | Thermal Decomposability |
| --- | --- | --- |
| Compound No. 2 | liquid | 140° C. |
| $TiCl_4$ | liquid | >300° C. |
| $TiCl[N(CH_3)_2]_3$ | solid (mp: 70° C.) | 140° C. |
| $Ti[N(CH_3)(C_2H_5)]_4$ | liquid | 200° C. |

As shown in Table 1, compound No. 2 of the invention, unlike the analogous compound $TiCl[N(CH_3)_2]_3$, is liquid at room temperature and therefore suitable as a material for chemical vapor phase growth. It is also seen that compound No. 2 exhibits higher thermal decomposability than $TiCl_4$ and $Ti[N(CH_3)(C_2H_5)]_4$. This suggests that compound No. 2 allows for thin film formation at a lower temperature and produces a thin film with better qualities. In particular, the thin film formed using compound No. 2 as a precursor has a reduced content of residual carbon that would affect electrical characteristics of the film so that the film is considered suited for use as a gate film, a barrier film, and an electrode film of LSI devices, typified by titanium nitride films.

TABLE 2

| Metal Compound | State | Thermal Decomposability |
| --- | --- | --- |
| Compound No. 6 | liquid | 100° C. |
| $TiCl_2[N(CH_3)_2]_2$ | solid (mp: 83° C.) | 100° C. |

As shown in Table 2, compound No. 6 of the invention, unlike the analogous compound $TiCl_2[N(CH_3)_2]_2$, is liquid at room temperature and therefore suitable as a material for chemical vapor phase growth. Compound No. 6 was equal to $TiCl_2[N(CH_3)_2]_2$ in thermal decomposability. As compared with compound No. 2, compound No. 6 decomposes at a lower temperature. However, having a decomposition temperature of 100° C. provides a small processing margin. Taking the margin between the volatilization temperature and the film formation temperature into consideration, compound No. 2 is more suitable than compound No. 6 for use in chemical vapor phase growth.

Example 3

Fabrication of Titanium Nitride Thin Film

A titanium nitride thin film was fabricated on a silicon wafer by ALD using the equipment illustrated in FIG. 1 and compound No. 2 obtained in Example 1 as a chemical vapor phase growth material under the conditions described below. The resulting film was analyzed by X-ray fluorometry to determine the film thickness and composition. It was found as a result that the film thickness was 60 nm, the film composition was titanium nitride, and the carbon content was 1.3 at %.
ALD Conditions:
Reaction temperature (substrate temperature): 300° C.
Reactive gas: $NH_3$
Three hundred cycles each having steps (1) to (4) were performed.
(1) A CVD material vaporized in the vaporizer at 120° C. and 250 Pa was pulsed into the deposition chamber and allowed to deposit for 3 seconds under a system pressure of 250 Pa.
(2) The chamber was purged with argon for 3 seconds to remove the unreacted material.
(3) The reactive gas was pulsed into the chamber and allowed to react for 3 seconds under a system pressure of 250 Pa.
(4) The chamber was purged with argon for 2 to remove the unreacted material.

Comparative Example 1

A titanium nitride thin film was fabricated on a silicon wafer by ALD using $Ti[N(CH_3)(C_2H_5)]_4$ as a chemical vapor phase growth material under the same conditions as in Example 2. The resulting film was analyzed by X-ray fluorometry to determine the film thickness and composition. It was found as a result that the film thickness was 50 nm, the film composition was titanium nitride, and the carbon content was 7.0 at %.

BRIEF DESCRIPTION OF THE DRAWING

FIG. 1 is a schematic illustration of an example of CVD apparatus used in the thin film formation according to the invention.

INDUSTRIAL APPLICABILITY

The invention provides a metal compound having physical properties suitable as a material for chemical vapor phase growth used in the formation of a metal-containing thin film, especially a metal nitride thin film.

The invention claimed is:

1. A metal compound represented by general formula (1):

[Formula 1]

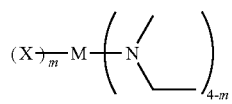
(1)

wherein M represents titanium, zirconium, or hafnium; X represents a halogen atom; and m represents 1 or 2.

2. The metal compound according to claim 1, wherein M is titanium.

3. The metal compound according to claim 1, wherein X is a chlorine atom.

4. The metal compound according to claim 1, wherein m is 1.

5. A material for chemical vapor phase growth comprising the metal compound according to claim 1.

6. The material for chemical vapor phase growth according to claim 5, which is for the formation of a metal nitride thin film on a substrate.

7. The metal compound according to claim 2, wherein X is a chlorine atom.

8. The metal compound according to claim 2, wherein m is 1.

9. The metal compound according to claim 3, wherein m is 1.

10. A material for chemical vapor phase growth comprising the metal compound according to claim 2.

11. A material for chemical vapor phase growth comprising the metal compound according to claim 3.

12. A material for chemical vapor phase growth comprising the metal compound according to claim 4.

13. The metal compound according to claim 7, wherein m is 1.

14. A material for chemical vapor phase growth comprising the metal compound according to claim 7.

15. A material for chemical vapor phase growth comprising the metal compound according to claim 8.

16. A material for chemical vapor phase growth comprising the metal compound according to claim 9.

* * * * *